US011780739B2

(12) United States Patent
Chang et al.

(10) Patent No.: US 11,780,739 B2
(45) Date of Patent: Oct. 10, 2023

(54) METHOD FOR PRODUCING IRON OXIDE MAGNETIC PARTICLES, AND IRON OXIDE MAGNETIC MATERIALS PREPARED THEREBY

(71) Applicant: ZTI Biosciences Co., Ltd., Daejeon (KR)

(72) Inventors: Hyungseok Chang, Seoul (KR); Sei Jin Park, Seoul (KR); Yong-Sun Park, Seoul (KR); Ji Young Ryu, Yongin-si (KR); Yoon-Sik Lee, Anyang-si (KR)

(73) Assignee: ZTI BIOSCIENCES CO., LTD., Daejeon (KR)

( * ) Notice: Subject to any disclaimer, the term of this patent is extended or adjusted under 35 U.S.C. 154(b) by 276 days.

(21) Appl. No.: 17/187,523

(22) Filed: Feb. 26, 2021

(65) Prior Publication Data
US 2021/0317005 A1    Oct. 14, 2021

(30) Foreign Application Priority Data

Apr. 13, 2020  (KR) .......................... 10-2020-0044724
Apr. 13, 2020  (KR) .......................... 10-2020-0044735

(51) Int. Cl.
*C01G 49/06*     (2006.01)
*H01F 1/00*      (2006.01)
(Continued)

(52) U.S. Cl.
CPC .......... *C01G 49/06* (2013.01); *H01F 1/0054* (2013.01); *H01F 1/342* (2013.01); *B82Y 5/00* (2013.01);
(Continued)

(58) Field of Classification Search
CPC ......... C01G 49/06; H01F 1/0054; B82Y 5/00; B82Y 25/00; B82Y 30/00; B82Y 40/00; C01P 2004/04; C01P 2006/42
See application file for complete search history.

(56) References Cited

U.S. PATENT DOCUMENTS 89,740 A   *   5/1869   Cyester ................. C07F 15/025
                                                    428/402.24
6,962,685 B2 * 11/2005   Sun ................... C04B 35/62826
                                                    423/632
(Continued)

FOREIGN PATENT DOCUMENTS

CN       105964282 A    *   9/2016   ............ B01J 27/128
JP       2011-516279 A       5/2011
(Continued)

OTHER PUBLICATIONS

Watt et al. ChemPlusChem 2017, 82, 347-351 (Year: 2017).*
(Continued)

*Primary Examiner* — Anthony J Zimmer
*Assistant Examiner* — Jordan W Taylor
(74) *Attorney, Agent, or Firm* — Sughrue Mion, PLLC

(57) ABSTRACT

The present invention provides a method for preparing iron oxide magnetic particles and iron oxide magnetic particles prepared thereby, wherein the method includes (a) synthesizing a complex by reacting iron and one or more compounds selected from the group consisting of an aliphatic hydrocarbonate having 4 to 25 carbon atoms and an amine compound, (b) synthesizing an iron oxide crystal nucleus by mixing the complex with a mixture of an unsaturated aliphatic hydrocarbon-based compound having 4 to 25 carbon atoms and an ether-based compound, and (c) forming a shell by mixing the iron oxide crystal nucleus and an MXn compound with a mixture of an unsaturated aliphatic hydrocarbon-based compound having 4 to 25 carbon atoms and an (Continued)

ether-based compound, wherein M is a heavy atom element, X is a halogen element, and n is an integer of 1 to 6.

5 Claims, 7 Drawing Sheets

(51) Int. Cl.
  *H01F 1/34* (2006.01)
  *B82Y 5/00* (2011.01)
  *B82Y 25/00* (2011.01)
  *B82Y 30/00* (2011.01)
  *B82Y 40/00* (2011.01)
(52) U.S. Cl.
  CPC .............. *B82Y 25/00* (2013.01); *B82Y 30/00* (2013.01); *B82Y 40/00* (2013.01); *C01P 2002/72* (2013.01); *C01P 2002/85* (2013.01); *C01P 2004/04* (2013.01); *C01P 2004/64* (2013.01); *C01P 2006/42* (2013.01)

(56) References Cited

U.S. PATENT DOCUMENTS

| | | | |
|---|---|---|---|
| 2018/0358155 A1* | 12/2018 | Naoi | C08L 101/06 |
| 2019/0023584 A1* | 1/2019 | Bae et al. | F24C 15/10 |
| | | | 126/211 |

FOREIGN PATENT DOCUMENTS

| | | |
|---|---|---|
| JP | 2013-534893 A | 9/2013 |
| JP | 2014-111600 A | 6/2014 |
| JP | 2014-528920 A | 10/2014 |
| JP | 2015-199726 A | 11/2015 |
| JP | 2019-536716 A | 12/2019 |
| KR | 10-2012-0013519 A | 2/2012 |
| KR | 10-2015-0092743 A | 8/2015 |
| KR | 10-2019-0010324 A | 1/2019 |

OTHER PUBLICATIONS

Mazurenko et al (Physics and Chemistry of Solid State, 2017, 18(2), 215-221.) (Year: 2017).*
Li et al. CN105964282A English Translation (Year: 2016).*
R.V. Mazurenko et al., "Synthesis, Electrical and Magnetic Properties of Composites Copper Iodide/Magnetite-Polychlorotrifluoroethylene", Physics and Chemistry of Solidstate, May 6, 2017, p. 215-221, V. 18, No. 2, Chuiko Institute of Surface Chemistry of the NAS of Ukraine, Ukraine.
Dipranjan Laha, et al., "Evaluation of copper iodide and copper phosphate nanoparticles for their potential cytotoxic effect", The Royal Society of Chemistry 2012, Mar. 14, 2012, Toxicol. Res., 2012, 1, 131-136, Department of Life Science and Biotechnology, Jadavpur University, Kolkata, India.
Fernandez-Barahona et al., "Cu-Doped Extremely Small Iron Oxide Nanoparticles with Large Longitudinal Relaxivity: One-Pot Synthesis and in Vivo Targeted Molecular Imaging", ACS Omega, 2019, vol. 4, pp. 2719-2727 (9 pages total).
Ebrahimisadr et al., "Magnetic Hyperthermia Properties of Iron Oxide Nanoparticles: The Effect of Concentration", Physica C: Superconductivity and its applications, 2018 (6 pages total).
Office Action dated Nov. 8, 2022 in Japanese Application No. 2021-569348.

* cited by examiner

INTRICSIC LOSS POWER (ILP) CHANGE GRAPH ACCORDING SOLVENT CONDITION

METHOD FOR PRODUCING IRON OXIDE MAGNETIC PARTICLES, AND IRON OXIDE MAGNETIC MATERIALS PREPARED THEREBY

CROSS-REFERENCE TO RELATED APPLICATION(S)

This application is based on and claims priority under 35 U.S.C. § 119 to Korean Patent Application No. 10-2020-0044724, filed on Apr. 13, 2020, and Korean Patent Application No. 10-2020-0044735, filed on Apr. 13, 2020, in the Korean Intellectual Property Office, the disclosure of which is incorporated by reference herein its entirety.

TECHNICAL FIELD

The present invention relate to a method for preparing iron oxide magnetic particles and iron oxide magnetic particles prepared thereby.

BACKGROUND ART

Magnetic materials have been widely used in the biomedical field including cell labeling, magnetic resonance imaging (MRI), drug delivery, and hyperthermia. Among various types of magnetic particles, superparamagnetic iron oxide-based particles have been widely researched on in the biomedical field due to high magnetic susceptibility and superparamagnetic properties thereof.

In addition, magnetic particles are characterized by generating heat when radiation or a magnetic field is applied thereto, and thus, may also be used as a contrast agent of a magnetic resonance imaging (MRI) device, a magnetic carrier for drug delivery in the nanomedicine field, or for magnetic or radiation-based thermal therapy, and the like.

In the imaging diagnosis field, an iron oxide is a superparamagnetic contrast agent, and is proposed as a negative contrast agent. However, an iron oxide has strong hydrophobic attraction, and thus, aggregates well with each other, thereby forming a cluster, or when exposed to a bio-environment and the iron oxide is subjected to quick bio-degradation and becomes not sufficiently stable, so that the original structure thereof may change, causing the change in magnetic properties thereof as well, and thus, has toxicity. On the other hand, iodine is proposed as a positive contrast agent, and when used in high concentration to increase the contrast effect, liver/kidney toxicity occurs. Therefore, a formulation technology for increasing the content per volume of a contrast medium is introduced.

Meanwhile, radiation-based or electromagnetic field-based thermotherapy has been proposed to overcome the limitations of typical cancer treatment methods (Wust et al. Lancet Oncology, 2002, 3:487-497). One of the unique properties of cancer cells is that the ability thereof to adapt to heat is significantly lower than that of normal cells. Thermotherapy is an anti-cancer therapy that selectively kills cancer cells by raising the temperature of cancer tissues and their surroundings to about 40 to 43° C.° using the difference in thermal sensitivity between normal cells and cancer cells. When a magnetic field is applied from the outside by injecting magnetic particles around cancer cells, heat is generated from the magnetic particles, so that the cancer cells may be killed in a short period of time. Since a magnetic field is not affected by skin tissues, there is no limit to the penetration depth of the magnetic field, so that heat may be selectively applied when magnetic particles are accumulated in cancer tissues in a body. Thus, research on thermotherapy using magnetic particles has attracted a lot of attention.

Iron oxide magnetic particles are mainly used as magnetic particles for thermotherapy. This is because iron oxide magnetic particles are a material having an indirect band gap in which energy as much as momentum used is converted into heat and released. Among them, $Fe_3O_4$ magnetic particles have bio-compatibility, heat-inducing ability, chemical stability, and unique magnetic properties, and thus, have been subjected to active research as a magnetic heating element, and have been approved for medical use by the FDA of the Unites States of America. However, $Fe_3O_4$ particles are easily changed to $\alpha$-$Fe_2O_3$, $\gamma$-$Fe_3O_4$, and the like depending on the conditions of the surrounding environment, and thus, have a disadvantage in that the exothermic properties and magnetic properties thereof change accordingly, resulting in the decrease in heat generation ability. As for other materials, research is being conducted on Co, Ni, and Mg-based $MFe_2O_4$(M=Co,Ni,Mg) particles. However, they also have a disadvantage in that it is difficult to apply the same in vivo due to a low exothermic temperature thereof.

PRIOR ART DOCUMENT

Non-patent literature: Wust et al. Lancet Oncology, 2002, 3:487-497

DISCLOSURE OF THE INVENTION

Technical Problem

The present invention has been devised in consideration of the circumstances described above, and provides a method for preparing iron oxide magnetic particles and iron oxide magnetic particles prepared thereby, which may be applied to various imaging diagnosis devices while having high structural stability, and which may be applied to various fields based on an exothermic effect when applied to specific radiation, magnetic fields and radio waves.

Technical Solution

In order to solve the above problem, the present invention provides a method for preparing iron oxide magnetic particles and iron oxide magnetic particles prepared thereby, wherein the method comprises (a) synthesizing a complex by reacting iron and one or more compounds selected from the group consisting of an aliphatic hydrocarbonate having 4 to 25 carbon atoms and an amine compound, (b) synthesizing an iron oxide crystal nucleus by mixing the complex with a mixture of an unsaturated aliphatic hydrocarbon-based compound having 4 to 25 carbon atoms and an ether-based compound, and (c) forming a shell by mixing the iron oxide crystal nucleus and an $MX_n$ compound with a mixture of an unsaturated aliphatic hydrocarbon-based compound having 4 to 25 carbon atoms and an ether-based compound, wherein M is a heavy atom element, X is a halogen element, and n is an integer of 1 to 6.

Advantageous Effects

A method or preparing iron oxide magnetic particles of the present invention may prepare iron oxide magnetic nanoparticle effectively.

Iron oxide magnetic particles prepared thereby may have high reactivity to a stimulus introduced from the outside, such as radiation, magnetic fields, and radio waves.

In addition, a contrast agent including the iron oxide magnetic particles may be applied to various imaging diagnosis devices, and sufficient images may be obtained by administering a small dose.

Furthermore, since the structural stability is high due to the bond formed between an iron oxide and a heavy atom-halogen compound, there is no risk of side effects which may be caused by each constituent component, and the toxicity is low, so that safe application to a human body is possible.

MODE FOR CARRYING OUT THE INVENTION

Figure 1:
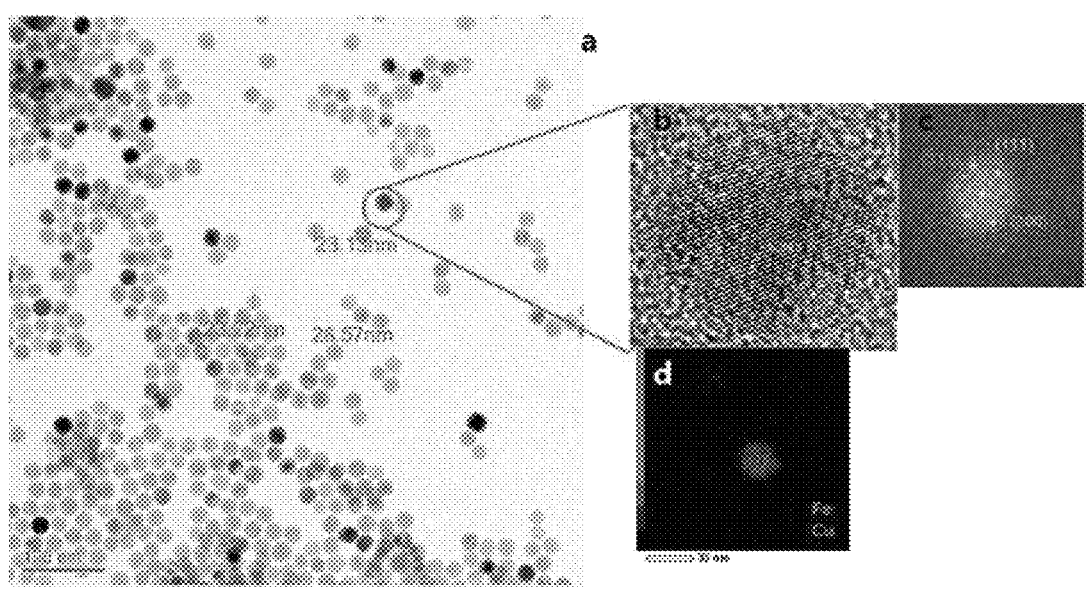
FIG. 1 illustrates the results of observing particles having a CuI/Fe3O4 core/shell structure synthesized according to an embodiment in the present invention using a transmission electron microscope (a: Transmission Electron Microscope (TEM) image, b: High-Resolution Transmission Electron Microscope (HR-TEM) image, c: Fast Fourier Transform (FTT) image, and d: Elemental mapping images for Fe and Cu elements). The thickness of the shell is about 1 to 3 nm.
Figure 2:
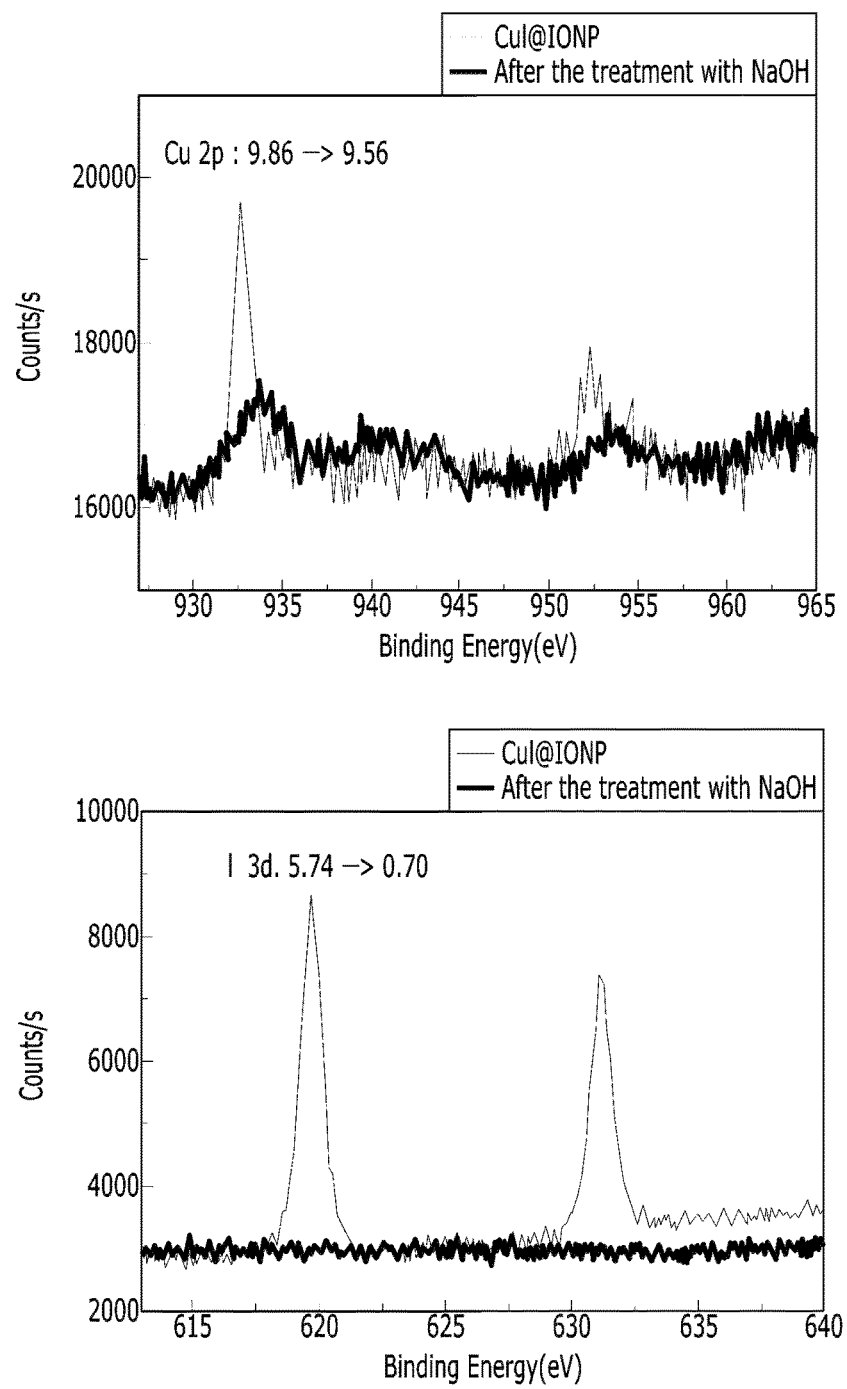
FIG. 2 illustrates the results of observing the dual structure of particles having a CuI/Fe3O4 core/shell structure synthesized according to an embodiment in the present invention using X-ray photoelectron spectroscopy. A peak due to a Cu 2p atomic orbital and an I 3d atomic orbital was detected in the particles according to the present invention. However, after the particles were treated with NaOH, which is a strong base, the peak due to the Cu 2p atomic orbital and the I 3d atomic orbital was not detected. It can be confirmed that a CuI shell is present on the surface of the particles according to the present invention, and that the CuI shell is removed after the treatment with NaOH.

Hereinafter, the present invention will be described in detail.

Method for Preparing Iron Oxide Magnetic Particles

A method for preparing iron oxide magnetic particles according to an embodiment of the present invention comprises (a) synthesizing a complex by reacting iron and one or more compounds selected from the group consisting of an aliphatic hydrocarbonate having 4 to 25 carbon atoms and an amine compound, (b) synthesizing an iron oxide crystal nucleus by mixing the complex with a mixture of an unsaturated aliphatic hydrocarbon-based compound having 4 to 25 carbon atoms and an ether-based compound, and (c) forming a shell by mixing the iron oxide crystal nucleus and an MXn compound with a mixture of an unsaturated aliphatic hydrocarbon-based compound having 4 to 25 carbon atoms and an ether-based compound, wherein M is a heavy atom element, X is a halogen element, and n is an integer of 1 to 6.

The term "iron oxide" refers to an oxide of iron, which may include, but is not limited to, for example, one or more selected from the group consisting of Fe13O19, Fe3O4 (magnetite), γ-Fe2O3 (maghemite), and α-Fe2O3 (hematite), β-Fe2O3 (beta phase), ε-Fe2O3 (epsilon phase), FeO (Wüstite), FeO2 (Iron Dioxide), Fe4O5, Fe5O6, Fe5O7, Fe25O32. and a delafossite.

The term "heavy atoms" refers to, for example, atoms heavier than B (boron), which belongs to M of MXn, and may specifically include one or more selected from the group consisting of Sn, Pb, Mn, Ir, Pt, Rh, Re, Ag, Au, Cu, Pd, and Os.

In an embodiment, the iron oxide may be derived from a complex of iron and one or more compounds selected from the group consisting of an aliphatic hydrocarbonate having 4 to 25 carbon atoms and an amine compound.

Examples of the aliphatic hydrocarbonate having 4 to 25 carbon atoms may include one or more selected from the group consisting of butyrate, valerate, caproate, enanthate, caprylic acid, pelargonate, caprate, laurate, myristate, pentadecylate, acetate, palmitate, palmitoleate, margarate, stearate, oleate, vaccenate, linoleate, (9,12,15)-linoleate, (6,9,12)-linoleate, eleostearate, tuberculasterate, larchidate, arachidonate, behenate, lignocerate, nervonate, serotate, montanate, melisate, and a peptide salt including one or more amino acids. A compound thereof may be used alone or in the form of two or more mixed acid salts.

A metal component of the salt may include one or more selected from the group consisting of calcium, sodium, potassium, and magnesium.

Examples of the amine compound may include one or more selected from the group consisting of methylamine, ethylamine, propylamine, isopropylamine, butylamine, amylamine, hexylamine, octylamine, 2-ethylhexylamine, nonylamine, decylamine, laurylamine, pentadecylamine, cetylamine, stearylamine, and cyclohexylamine, dimethylamine, diethylamine, dipropylamine, diisopropylamine, dibutylamine, diamylamine, dioctylamine, di(2-ethylhexyl)amine, didecylamine, dilaurylamine, dicetylamine, distearylamine, methylstearylamine, ethylstearylamine, and butylstearylamine, triethylamine, triamylamine, trihexylamine and trioctylamine, triallylamine and oleylamine, laurylaniline, stearylaniline, triphenylamine, N,N-dimethylaniline and dimethylbenzylaniline, monoethanolamine, diethanolamine, triethanolamine, dimethylaminoethanol, diethylenetriamine, triethylene tetramine, tetraethylenepentaamine, benzylamine, diethylaminopropylamine, xylylenediamine, ethylenediamine, hexamethylenediamine, dodecamethylenediamine, dimethylethylenediamine, triethylenediamine, guanidine, diphenylguanidine, N,N,N',N'-tetramethyl-1,3-butanediamine, N,N,N',N'-tetramethylethylenediamine, 2,4,6-tris(dimethylaminomethyl)phenol, morpholine, N-methylmorpholine, 2-ethyl-4-methylimidazole and 1,8-diazabicyclo (5,4,0)undecene-7 (DBU).

The unsaturated aliphatic hydrocarbon-based compound having 4 to 25 carbon atoms may include one or more selected from the group consisting of butene, pentene, hexene, heptene, octene, nonene, decene, undecene, dodecene, tridecene, tetradecene, pentadecene, hexadecene, heptadecane, and octadecene, and may preferably be octadecene, more preferably 1-octadecene.

The ether-based compound may include one or more selected from the group consisting of diethyl ether, tetrahydrofuran, dibutyl ether, dioxane, tetraethylene glycol dimethyl ether, and dibenzyl ether, and may preferably be dibenzyl ether.

The X is a halogen, and may include one or more selected from the group consisting of F, Cl, Br and I. In addition, the X may include a radioactive isotope of X or a mixture of radioactive isotopes of X. Specifically, it refers to a compound in which one or more atoms are replaced by an atom having the same atomic number but having atomic mass or mass number different from the atomic mass or mass number commonly found in nature. Examples of isotopes suitable to be included in the compound of the present invention are isotopes of fluorine, for example, 18F, isotopes of chlorine, for example, 36Cl, isotopes of bromine, for example, 75Br, 76Br, 77Br, and 82Br, and isotopes of iodine, for example, 123I, 124I, 125I, and 131I, alone or in combination.

Particles including MXn in the iron oxide particles have magnetism, and may amplify the contrast effect of an iron oxide under relatively low alternating magnetic field intensity and/or a low frequency magnetic field.

The iron oxide magnetic particles of the present invention have a predetermined preparation step in each of Steps (a) to (c), and may be specifically prepared through (a) adding a precursor metal complex, a stabilizer, and a dispersant to an organic solvent to prepare a mixed solution, (b) pyrolyzing the mixed solution below the boiling point of an organic solvent used for synthesis to form a crystal nucleus (nucleation), and (c) forming a crystal structure through a growth step of the crystal nucleus.

When the temperature is raised to the boiling point of the solvent, the precursor is pyrolyzed to form a monomer, and growth occurs after the formation of a crystal nucleus. The growth step of particles is determined by a reaction rate factor of the surface of the crystal nucleus and a diffusion factor of the monomer. Under a reaction temperature condition, most precursors are pyrolyzed. At this time, a heavy atom-halogen compound having a high melting point is not decomposed, so that material diffusion is relatively slow compared to other monomers. Accordingly, the heavy atom-halogen compound is present on the surface of the particles in a crystallization process, and as a result, a core/shell dual structure in which an iron oxide is present thereinside and the heavy atom-halogen compound is present thereoutside is synthesized.

As the nanomaterial precursor, a metal nitrate-based compound, a metal sulfate-based compound, a metal acetylacetonate-based compound, a metal fluoroacetoacetate-based compound, a metal halide-based compound, a metal perchlorate-based compound, and a metal alkyloxide-based compound, a metal sulfamate-based compound, a metal stearate-based compound, or an organic metal-based compound may be used, but the present invention is not limited thereto.

The iron oxide magnetic particles of the present invention have very stable bonds between iron oxide particles and a heavy atom-halogen compound and between heavy atom-halogen, so that there is little risk of side effects which may be caused by each constituent component, that is, an iron oxide, a heavy atom, and a halogen element.

The iron oxide magnetic particles of the present invention may be prepared by including the MXn in an amount of about 1 to 13 mol %, preferably about 1 to 8 mol %, based on 100 mol % of a complex formed with one or more compounds selected from the group consisting of an aliphatic hydrocarbonate having 4 to 25 carbon atoms and an amine compound.

According to an embodiment of the present invention, the MXn includes one or more selected from the group consisting of CuI, CuF, CuBr, CuCl, SnI, SnF, SnBr, SnCl, PbI, PbF, PbBr, PbCl, MnI, MnF, MnBr, and MnCl, and n may be an integer of 1 to 6.

The volume % of the unsaturated aliphatic hydrocarbon-based compound having 4 to 25 carbon atoms in the mixture of an unsaturated aliphatic hydrocarbon-based compound having 4 to 25 carbon atoms and an ether-based compound used in Step (c) may be 25 to 75 vol %. When the above range is satisfied, an excellent self-induced heating ability may be ensured.

According to the present invention, a step of coating the surface of particles prepared after Step (c) with a hydrophilic ligand may be further included. In an embodiment, the iron oxide magnetic particles may be that at least a portion of the surface of the iron oxide particles is coated with a hydrophilic ligand. The hydrophilic ligand may be introduced to increase the solubility of the iron oxide magnetic particles according to an embodiment in water and increase stabilization, or to enhance targeting or penetration for specific cells, such as cancer cells. Such a hydrophilic ligand may preferably have bio-compatibility, and may include, for example, one or more selected from the group consisting of polyethylene glycol, polyethylene amine, polyethylene imine, polyacrylic acid, polymaleic anhydride, polyvinyl alcohol, polyvinylpyrrolidone, polyvinyl amine, polyacrylamide, polyethylene glycol, phosphate-polyethylene glycol, polybutylene terephthalate, polylactic acid, polytrimethylene carbonate, polydioxanone, polypropylene oxide, polyhydroxyethyl methacrylate, starch, dextran derivative, silica, and polypeptide, but is not limited thereto.

If necessary, when targeting cancer cells, it is possible to use folic acid, transferrin, or RGD peptide as the hydrophilic ligand, and hyaluronidase or collagenase may be used to enhance penetration into cells, but the hydrophilic ligand is not limited thereto.

Iron Oxide Magnetic Particles

According to an embodiment of the present invention, iron oxide magnetic particles formed according to the above preparation method may include a core made of an iron oxide and MXn formed on the surface of the core.

The iron oxide magnetic particles may be used at a frequency of 1 kHz to 1 Mhz, or in a magnetic field having an intensity of 20 Oe (1.6 kA/m) to 200 Oe (16.0 kA/m).

The iron oxide magnetic particle may have an average particle diameter (d50) between 0.1 nm and 1 μm. If the size of the iron oxide magnetic particle has an average particle diameter (d50) between 0.1 nm and 100 nm, the iron oxide magnetic particle can be used as a component of a contrast medium, an anti-cancer agent, a thermal therapeutic agent, or a radiotherapeutic agent. If the size of the iron oxide magnetic particle exceeds 100 nm, the iron oxide magnetic can be applied in various fields of in vitro medicine. When the iron oxide magnetic particles of the present invention are used in a composition for thermotherapy, if the particle size of the iron oxide magnetic particles is about 15 nm or less, intravenous injection is preferable, and if about 15 nm or greater, intralesional and intratumor injections are preferable. However, when administering the composition in vitro, such as in the thermotherapy for skin cancer, any nanomaterial size is possible.

The iron oxide magnetic particles of the present invention includes the MXn in about 5 to 50 vol %, preferably about 10 to 30 vol %.

The iron oxide magnetic particles as described above may ensure high specific loss power while having high reactivity to a stimulus introduced from the outside, such as radiation, magnetic fields, and radio waves, and thus, may be effectively used for thermotherapy to be described later.

Presumably, in the case of a heavy atom-halogen compound such as MXn, the dielectric constant and capacitance vary depending on the type of the heavy atom and the type of halogen (as an atomic shell grows from F to I on the periodic table, there is a difference in dielectric constant/electron capacitance), so that by bonding the compound with an iron oxide, which is a magnetic body, it is possible to increase magnetic strength, and by increasing the size or total amount of electromagnetic field energy that the compound may absorb, it is possible to increase the amount of thermal energy emitted by final iron oxide-based magnetic particles. This may improve or increase the high thermal energy emission (conversion) efficiency (ILP: Intrinsic loss power) compared to typical iron oxide-based magnetic particles, not only in a typical high-frequency (200 kHz or more) range, but also in an electromagnetic field energy environment of low-frequency and medium-frequency (50 Hz to 200 kHz) bands, which are relatively low.

In addition, a contrast agent including the iron oxide magnetic particles may be applied to various imaging diagnosis devices, and sufficient images may be obtained by administering a small dose.

Furthermore, since the structural stability is high due to the bond formed between an iron oxide and a heavy atom-halogen compound, there is no risk of side effects which may be caused by each constituent component, and the toxicity is low, so that safe application to a human body is possible. In addition, a heavy atom-halogen compound stabilizes various halogens, especially an iodine group among others, compared to an alkali-halogen compound, so that iodine-based medicines or radioactive isotopes used as typical drugs may be efficiently fixed on an iron oxide, which enables typical iodine-based medicines or radiation medicines to be efficiently delivered to an affected area to treat the same, and to be easily discharged.

The iron oxide magnetic particles according to an embodiment of the present invention may be used as a contrast agent, or may be used for thermal or radiation-based treatment to kill cancer cells. In addition, it may be used in a composition for bio-imaging including the above-described iron oxide magnetic particles. The iron oxide magnetic particles according to the present invention have magnetism, and thus, may be used as a contrast agent for diagnosis useful in diagnostic methods using electromagnetic properties including radiation (X-ray, CT, MRI, PET-CT, and the like).

According to an embodiment of the present invention, the present invention provides a method for diagnosing cancer, wherein the method includes the steps of (1) administering a composition including the iron oxide magnetic particles to a cancer suspect patient, and (2) detecting the presence of magnetic particles in the patience by using a magnetic resonance device. When the magnetic particles according to the present invention are administered, for example, the contrast between a lesion and a normal tissue may be clearly enhanced and visualized in MRI T1 and T2-weighed images, and a contrast effect efficient may be confirmed even in a low-dose radiation dose of radiation-based imaging equipment such as X-ray, CT, and PET-CT. When the iron oxide magnetic particles of the present invention are administered, it is possible to diagnose cancer without separately administering an additional contrast agent, so that cancer diagnosis and treatment may be simultaneously performed using the iron oxide magnetic particles of the present invention.

If the iron oxide magnetic particles of the present invention are bonded with a cancer cell targeting material or a penetration enhancing material, it is possible to perform thermal diagnosis and treatment more efficiently under an external alternating magnetic field. In the present invention, a "cancer cell targeting material" may include a peptide including various antibodies, aptamer, folic acid, transferrin, and RGD, but is not limited thereto.

In an embodiment, the contrast agent may include 0.1 to 15 wt %, 1 to 15 wt %, 1 to 10 wt %, 3 to 10 wt %, or 4 to 8 wt % of iron oxide magnetic particles based on the total contrast agent composition.

When iron oxide magnetic particles are included within the range described above, the iron oxide magnetic particles are discharged to the outside of a body without being accumulated in the body, and thus, may significantly reduce toxicity as a contrast agent.

In an embodiment, the contrast agent may exhibit a contrast effect in a magnetic field having a frequency of 1 kHz to 1 MHz or an intensity of 20 Oe (1.6 kA/m) to 200 Oe (16 kA/m). An alternating magnetic field which is irradiated after the contrast agent is administered to an individual may have a frequency of 1 kHz to 1 MHz, or a frequency of 30 kHz to 120 kHz. In general, in order to convert the spin state from singlet to triplet, an alternating magnetic field of 1 MHz or greater should be applied. However, in the case of the present invention, triplet interconversion is possible even under an alternating magnetic field of tens to hundreds of kHz. In addition, an alternating magnetic field may have a magnetic field intensity of 20 Oe (1.6 kA/m) to 200 Oe (16.0 kA/m), 80 Oe (6.4 kA/m) to 160 Oe (12.7 kA/m), or 140 Oe (11.1 kA/m). The contrast agent according to an embodiment is useful in that it may be used in an alternating magnetic field having a low magnetic field intensity and/or frequency, which is relatively harmless to a human body, unlike a typical high-energy method.

The contrast agent of the present invention is characterized by not being limited to a device which may be applied for image diagnosis. The contrast agent of the present invention has both a negative contrast agent component and a positive contrast agent component, and thus, has a high degree of contrast, thereby exhibiting an excellent contrast effect. For example, X-ray images, Magnetic Resonance Imaging (MRI), Computed Tomography (CT), US, optical images, Single Photon Emission Computed Tomography (SPECT), Positron Emission Tomography (PET)-CT, and flat panel images, and rigid, flexible, or capsule endoscopy, but is not limited thereto. Not being limited to a device which may be used as a contrast agent may be very useful when a complex test is required. For example, when a CT scan and an MRI scan are to be conducted within a short period of time, if a CT contrast agent and an MRI contrast agent are mixed in the body of an individual, test result may not be clear, and when the individual are administered with a different contrast agent for each test, the probability of causing toxicity increases. However, the contrast agent of the present invention may be applied to various devices in combination, so that it is possible to reduce such inconvenience.

Another aspect provides a composition for diagnosing a cancer, wherein the composition includes the contrast agent according to an embodiment.

The cancer may be stomach cancer, lung cancer, melanoma, uterine cancer, breast cancer, ovarian cancer, liver cancer, biliary tract cancer, gallbladder cancer, bronchial cancer, nasopharyngeal cancer, laryngeal cancer, pancreatic cancer, bladder cancer, colon cancer, rectal cancer, colorectal cancer, cervical cancer, brain cancer, prostate cancer, bone cancer, skin cancer, blood cancer, kidney cancer, prostate cancer, thyroid cancer, parathyroid cancer, or ureteral cancer.

The composition for diagnosing a cancer may be administered to an individual in an oral or parenteral manner, and may include a pharmaceutically acceptable carrier to be suitable for each administration. Suitable pharmaceutically acceptable carriers and medicines are described in detail in a Remington's book (Remington's Pharmaceutical Sciences 19th ed., 1995).

When the composition for diagnosing a cancer is administered in an oral manner, it may be administered as a solid medicine such as tablets, capsules, pills, or granules, or as a liquid medicine such as solutions and suspensions.

When the composition for diagnosing a cancer is administered in a parenteral manner, it may be administered by intravenous injection, subcutaneous injection, intramuscular injection, intraperitoneal injection, intralesional injection, intratumoral injection, and the like.

When the composition for diagnosing a cancer is administered orally or parenterally as a liquid, it may be prepared as an aqueous solution or a suspension using a commonly known solvent such as isotonic sodium chloride solution, Hank's solution, or Ringer's solution.

In an embodiment, the composition for diagnosing a cancer may be for treating a cancer at the same time.

As described above, the contrast agent of the present invention is a thermotherapy method based on electromagnetic fields or radiation, and may ultimately kill cancer cells. The term "thermotherapy" means a next-generation cancer treatment method which kills lesion cells as well as cancer cells by exposing body tissues to a temperature higher than a normal body temperature, or allows such cells to have higher sensitivity to radiation therapy or anticancer drugs, thereby increasing treatment efficiency. Cancer thermotherapy based on electromagnetic fields or radiation includes whole body hyperthermia, which increases a cancer treatment effect in combination with radiation therapy/drug therapy, and loco-regional hyperthermia, which kills cancer cells by injecting magnetic particles into a targeted solid cancer and then applying an external alternating magnetic field thereto.

As described above, a thermotherapy method has an advantage in that cancer cells may be selectively killed, thereby lowering side effects. However, a thermotherapy technology based on typical magnetic particles has a problem in that the caloric value of the particles themselves caused by an external alternating magnetic field or radiation irradiation equipment is low and the persistence thereof is limited, so that it has been pointed out that there is a limit in thermotherapy. Typically, in order to solve the above problem, the following two methods have been used:

(a) a method of increasing the intensity or frequency of an external alternating magnetic field or radiation in order to increase the exothermic phenomenon of particles, or (b) a method of increasing the concentration of particles to be injected in vivo.

However, (a) the method of increasing the intensity or frequency of an external alternating magnetic field or radiation may cause red spots to appear around the skin and slight burns, wounds, inflammation, necrosis, and the like to appear in fatty areas, and may also damage not only cancer tissues, but also normal tissue cells, thereby lowering immunity. In addition, the method is prohibited for use in pregnant women, patients with severe inflammation, patients with cardiac pacemaker vegetation, and patients with severe hydrothorax and hydrops abdominis because side effects due to human harmfulness are unavoidable. Moreover, due to various side effects thereof, high-dose radiation is strictly limited in its repetitive use. As an alternative, there have been efforts to improve efficiency by injecting iron oxide-based particles in vivo. However, (b) there have been problems in which the probability of accumulating particles in a body is increased and a toxicity problem due to the chemical composition of the surface of the particles occurs.

However, due to the internal quantum efficiency amplification effect of the iron oxide due to the difference in dielectric constant or electron capacitance caused by a bonded halogen group, the iron oxide magnetic particles according to the present invention result in efficient heat generation when used in thermotherapy using an external alternating magnetic fields or radiation equipment. Accordingly, the concentration of particles to be injected in vivo may be significantly lowered compared to typical iron oxide-based particles, and thus, problems of bio-accumulation and toxicity may be greatly reduced. In conclusion, the present invention may significantly overcome the disadvantages of the prior art which has been limited in use due to a low calorific value, despite the advantages of bio-compatibility, chemical stability, magnetic properties of iron oxide magnetic particles.

Hereinafter, Examples and the like will be described in detail to facilitate understanding of the present invention. However, Examples according to the present invention may be modified into other various forms, and the scope of the present invention should not be construed as being limited to Examples described below. Examples of the present invention are provided to more fully describe the present invention to those skilled in the art.

EXAMPLES

Example 1: Synthesis of Particles Having $CuI/Fe_3O_4$ Core/Shell Structure

As an example of the iron oxide magnetic particles described herein, particles having a composition in which the volume % of ODE in a mixture of 1-octadecene (ODE) and dibenzyl ether (DBE), a solvent of an MXn compound used in the shell synthesis step, were synthesized by the following method.

(a) Synthesis of Iron-Oleic Acid Complex $FeCl_3 \cdot 6H_2O$ (30 mmol) and sodium oleate (28 mmol) were mixed with 200 ml of hexane, 100 ml of ethanol, and 100 ml of deionized water, and reacted while being vigorously stirred at 110° C. for 6 hours. The reaction solution was cooled at room temperature, and then a transparent lower layer thereof was removed using a separatory funnel. 100 ml of water was mixed with a brown upper organic layer and shaken, and then a lower water layer was removed again. The above was repeated for three times. The remaining brown organic layer was transferred to a beaker and heated at 110° C. for 4 hours to allow hexane to evaporate.

(b) Synthesis of Iron Oxide Nucleus 4.5 g (5 mmol) of iron-oleic acid or iron-oleamine complex and 0.7 g (2.5 mmol) of oleic acid were mixed with 5 ml of 1-octadecene (ODE) and 5 ml of dibenzyl ether (DBE). The mixture was placed in a round bottom flask, and gas and moisture were removed at 90° C. for about 30 minutes in a vacuum state. Nitrogen was injected thereto, and the temperature was raised to 200° C. Thereafter, the temperature was raised to 250° C. at a rate of 1° C./min and then a reaction was performed for 60 minutes. The reaction solution was cooled, and then transferred to a 50 ml conical tube. 30 ml of ethanol and hexane were injected in a 2:1 ratio, followed by centrifugation to precipitate particles. The precipitated particles were washed with 10 ml of hexane and 5 ml of ethanol, and then an obtained precipitate was dispersed in hexane.

(c) Synthesis of Iron Oxide Magnetic Particles Having CuI/Fe3O4 Core/Shell Structure 150 mg of 5 nm iron oxide crystal nucleus dispersed in 7 ml of hexane, 1.68 g (6 mmol) of oleic acid, and 0.025 g (0.15 mmol) of CuI were mixed with a mixed solution of 10 ml of 1-octadecene (ODE) and 10 ml of dibenzyl ether (DBE). The mixture was placed in a round bottom flask, and hexane was removed at 100° C. for about 30 minutes in a vacuum state. Nitrogen was injected thereto, and the temperature was raised to 200° C. Thereafter, the temperature was raised to 320° C. at a rate of 5° C./min and then a reaction was performed for 30 minutes. The reaction solution was cooled, and then transferred to a 50 ml conical tube. 30 ml of ethanol and hexane were injected in a 1:1 ratio, followed by centrifugation to precipitate particles. The precipitated particles were washed with 10 ml of hexane and 5 ml of ethanol, and then an obtained precipitate was dispersed in toluene or hexane.

The ODE volume % in the mixed solution of ODE and DBE used in Step (c) of Example 1 was 50 vol %. By adjusting ODE volume % to 0% (ODE 0 ml, DBE 20 ml), 25% (ODE 5 ml, DBE 15 ml), 75% (ODE 15 ml, DBE 5 ml), and 100% (ODE 20 ml, DBE 0 ml), a variety of particles were prepared.

Example 2: Preparation of Magnetic Particles Coated with Hydrophilic Polymer 2 g of polyacrilic acid and 40 ml of tetraethylene glycol were heated at 110° C., and then 150 mg of iron oxide magnetic particles dispersed in 5 ml of hexane was injected thereto with a syringe. This was stirred and reacted at 280° C. for 6 hours. The reaction solution was cooled, and then 20 ml of diluted HCl of 0.01 M was added thereto to collect particles attracted to a magnet. After repeating the above twice, a precipitate was obtained using ethanol and was finally dispersed in water.

Example 3: Analysis of Temperature Change According to Volume % of ODE in Solvent (Mixed Solution of 1-Octadecene (ODE) and Dibenzyl Ether (DBE)) of $MX_n$ Compound Used in Shell Synthesis Step Under External Alternating Magnetic Field A system for heating by inducing an alternating magnetic field consists of four main subsystems; (a) A variable frequency and amplitude sine wave function generator (20 MHz Vp-p, TG2000, Aim TTi, USA)), (b) A power amplifier (1200 Watt DC Power Supply, QPX1200SP, Aim TTi, USA), (c) An induction coil (rotation number: 17, diameter: 50 mm, height: 180 mm) and a magnetic field generator (Magnetherm RC, nanoTherics, UK), and (d) A temperature change thermocouple (OSENSA, Canada).

Figure 3:
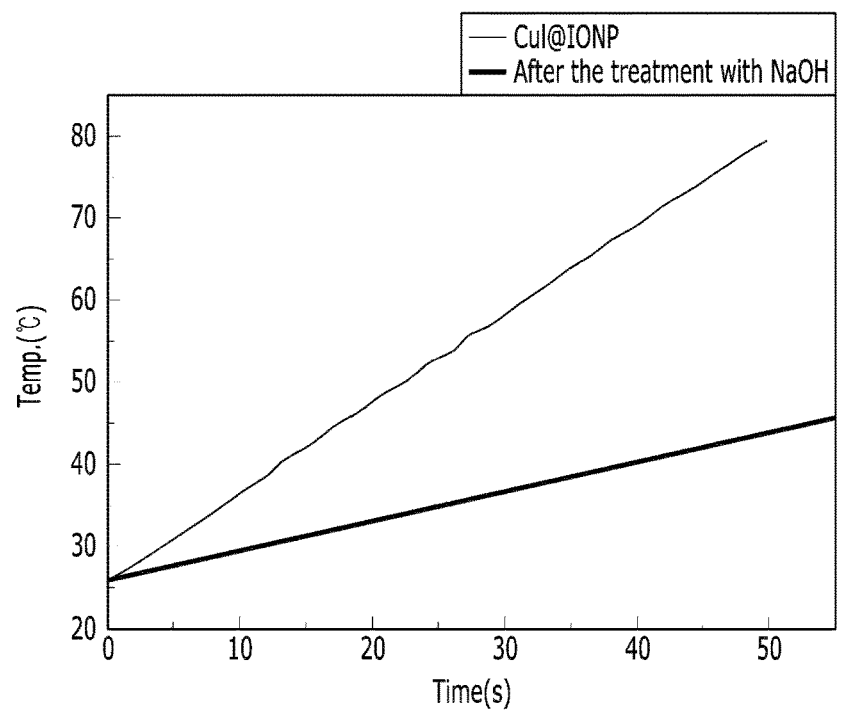
FIG. 3 is a graph showing changes in temperature over time after applying an external alternating magnetic field to particles having a CuI/Fe3O4 core/shell structure and to particles obtained by treating the particles with NaOH, which is a strong base, to remove a CuI shell.
Figure 4:
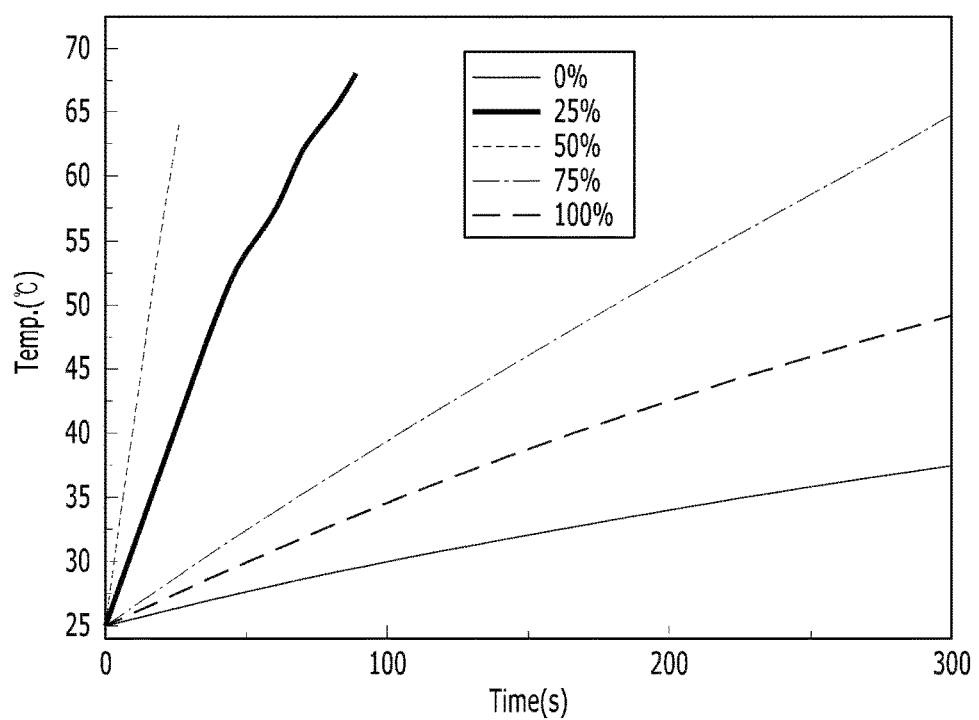
FIG. 4 is a graph showing changes in temperature over time after applying an external alternating magnetic field to particles having a CuI/Fe3O4 core/shell structure prepared by varying the volume % of ODE in a solvent (a mixture of 1-octadecene (ODE) and dibenzyl ether (DBE)) of an MXn compound used in the shell synthesis step according to an embodiment in the present invention.

Magnetic particles having an iron oxide/CuI core/shell structure were prepared as described above. The iron oxide magnetic particles were diluted to a concentration of 2 mg/ml in deionized water, and then an alternating magnetic field was applied thereto to measure the temperature change using a thermocouple (OSENSA, Canada). As a result, it was confirmed that the temperature was significantly increased when the magnetic particles having an iron oxide/CuI core/shell structure induced an alternating magnetic field (FIG. 3) compared to a control group of iron oxide particles (IONP) treated with a strong base (NaOH), thereby not including a shell. In addition, compared to the control group of iron oxide particles, in iron oxide magnetic particles in which CuI was coated with a shell, the self-induced heating ability was more excellent in the order of the ODE vol % of 50%, 25%, 75%, and 100% (FIG. 4).

Example 4: Measurement of Specific Loss Power (SLP)

The calorific value of particles varies depending on the physical and chemical properties, and the intensity and frequency of an external alternating magnetic field, most research results represent the heating ability of particles as SLP and ILP. SLP is electromagnetic force lost per mass unit and is represented by W (watts) per kg. Since the conditions of f (frequency) and H (magnetic field intensity) may be different for each experiment, it is possible to compare thermotherapy effects between particles by converting an SLP value to an ILP value using the equation $[ILP=SLP/(f \cdot H2)]$.

SLP was measured by using an alternating magnetic field generator (Magnetherm RC, Nanotherics) of a series resonance circuit controlled by a pickup coil and an oscilloscope. The measurement was performed under the thermal insulation condition of f=108.7 kHz and H=11.4 kA/m, and the temperature was measured using an optical fiber IR probe.

Figure 5:
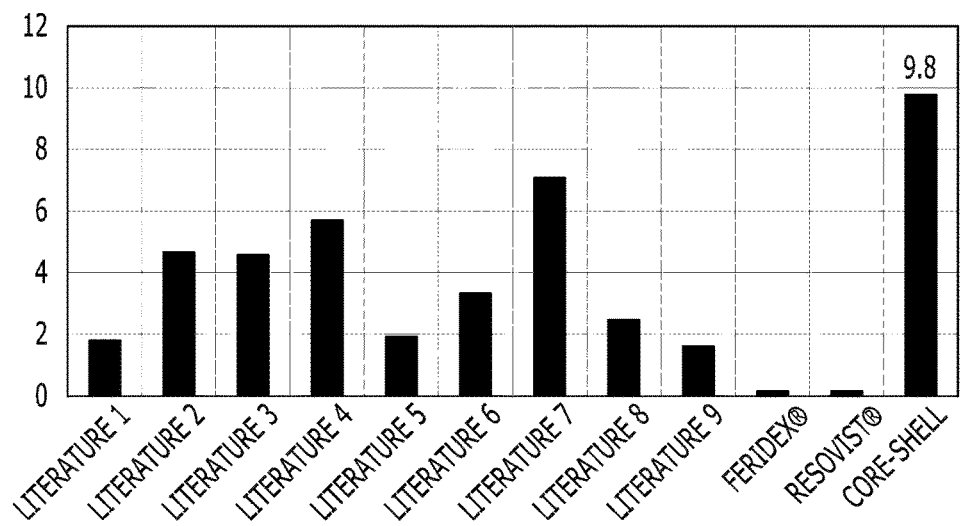
FIG. 5 is a graph showing ILP values after applying an external alternating magnetic field to CuI/Fe3O4 particles prepared by varying the volume % of ODE in a solvent (a mixture of ODE and DBE) of an MXn compound used in the shell synthesis step according to an embodiment in the present invention.

Iron oxide magnetic particles coated with polyacrilic acid were prepared as described above. SLP was measured by adjusting the magnetic particles to a concentration of 20 mg/ml. As a result, it was confirmed that iron oxide magnetic particles in which CuI was coated with a shell generated high ILP under an alternating magnetic field compared to the control group of iron oxide magnetic particles not including a shell (FIG. 5). The self-induced heating ability was more excellent in the order of the ODE vol % of 50%, 25%, 75%, and 100% in the solvent of an MXn compound used in the shell synthesis step.

Figure 6:
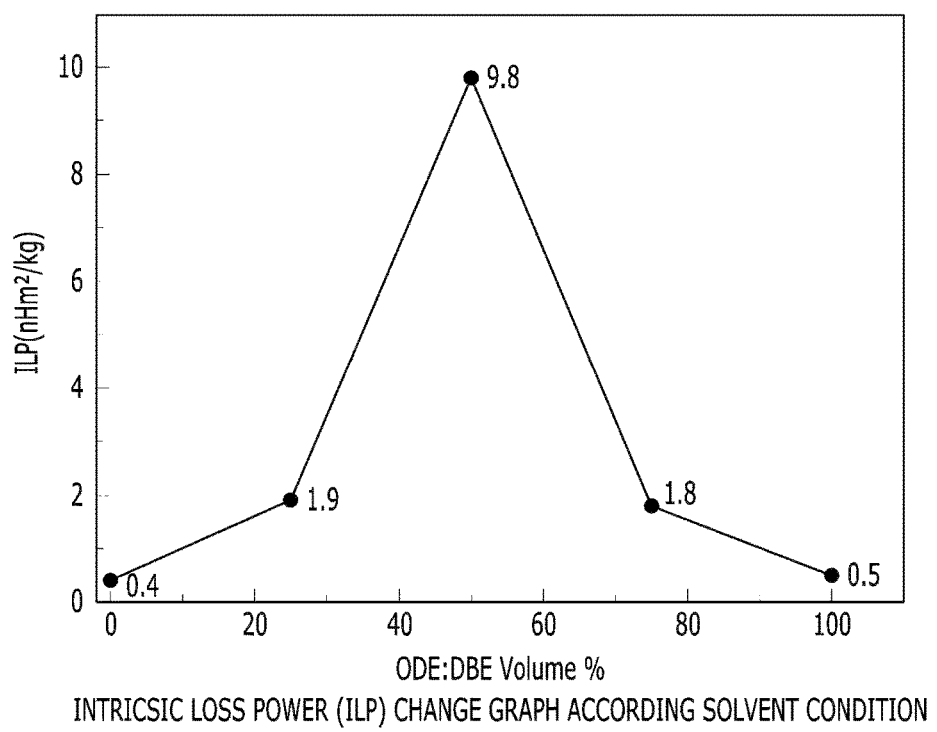
FIG. 6 is a graph comparing ILP values between particles according to an embodiment of the present invention and representative materials known in the art.

FIG. 6 is a graph comparing ILP values with representative materials known in the art, and specific ILP values are shown in Table 1. According to Table 1, it can be confirmed that the ILP value of the particles according to an embodiment of the present invention is increased by about 40% to 6100% compared to that of particles known in the art.

TABLE 1

| Sample name | ILP value |
| --- | --- |
| Literature 1 | 1.75 |
| Literature 2 | 4.52 |
| Literature 3 | 4.48 |
| Literature 4 | 5.6 |

TABLE 1-continued

| Sample name | ILP value |
|---|---|
| Literature 5 | 1.84 |
| Literature 6 | 3.23 |
| Literature 7 | 7.04 |
| Literature 8 | 2.33 |
| Literature 9 | 1.47 |
| Feridex ® | 0.16 |
| Resovist ® | 0.21 |
| Particles according to the present invention | 9.8 |

[Sample Source for Comparison]

| Sample | Literature title |
|---|---|
| Literature 1 | [Lv, Y.; Yang, Y.; Fang, J.; Zhang, H.; Peng, E.; Liu, X.; Xiao, W.; Ding, J. Size Dependent Magnetic Hyperthermia of Octahedral Fe3o4 Nanoparticles. RSC Adv. 2015, 5, 76764-76771.] |
| Literature 2 | [Liu, X. L.; Yang, Y.; Ng, C. T.; Zhao, L. Y.; Zhang, Y.; Bay, B. H.; Fan, H. M.; Ding, J. Magnetic Vortex Nanorings: A New Class of Hyperthermia Agent for Highly Efficient in Vivo Regression of Tumors. Adv. Mater. 2015, 27, 1939-1944.] |
| Literature 3 | [Yang, Y.; Liu, X.; Lv, Y.; Herng, T. S.; Xu, X.; Xia, W.; Zhang, T.; Fang, J.; Xiao, W.; Ding, J. Orientation Mediated Enhancement on Magnetic Hyperthermia of Fe3o4nanodisc. Adv. Funct. Mater. 2015, 25, 812-820.] |
| Literature 4 | [Martinez-Boubeta, C.; Simeonidis, K.; Makridis, A.; Angelakeris, M.; Iglesias, O.; Guardia, P.; Cabot, A.; Yedra, L.; Estrade, S.; Peiro, F.; Saghi, Z.; Midgley, P. A.; Conde-Leboran, I.; Serantes, D.; Baldomir, D. Learning from Nature to Improve the Heat Generation of Iron-Oxide Nanoparticles for Magnetic Hyperthermia Applications. Sci Rep. 2013, 3, 1652.] |

-continued

| Sample | Literature title |
|---|---|
| Literature 5 | [Peng, E.; Choo, E. S.; Chandrasekharan, P.; Yang, C. T.; Ding, J.; Chuang, K. H.; Xue, J. M. Synthesis of Manganese Ferrite/Graphene Oxide Nanocomposites for Biomedical Applications. Small. 2012, 8, 3620-3630.] |
| Literature 6 | [Lee, J.-H.; Jang, J.-t.; Choi, J.-s.; Moon, S. H.; Noh, S.-h.; Kim, J.-w.; Kim, J.-G.; Kim, I.-S.; Park, K. I.; Cheon, J. Exchange-Coupled Magnetic Nanoparticles for Efficient Heat Induction. Nat. Nanotechnol. 2011, 6, 418-422.] |
| Literature 7 | [Muela, A.; Muoz, D.; Martin-Rodriguez, R.; Orue, I.; Garaio, E.; Abad Diaz de Cerio, A.; Alonso, J.; Garcia, J..; Fdez-Gubieda, M. L. Optimal Parameters for Hyperthermia Treatment Using Biomineralized Magnetite Nanoparticles: Theoretical and Experimental Approach. J. Phys. Chem. C. 2016, 120, 24437-24448.] |
| Literature 8 | [Alphandry, E.; Chebbi, I.; Guyot, F.; Durand-Dubief, M. Use of Bacterial Magnetosomes in the Magnetic Hyperthermia Treatment of Tumours: A Review. Int. J. Hyperthermia. 2013, 29, 801-809.] |
| Literature 9 | [Niculaes, D.; Lak, A.; Anyfantis, G. C.; Marras, S.; Laslett, O.; Avugadda, S. K.; Cassani, M.; Serantes, D.; Hovorka, O.; Chantrell, R.; Pellegrino, T. Asymmetric Assembling of Iron Oxide Nanocubes for Improving Magnetic Hyperthermia Performance. ACS Nano. 2017, 11, 12121-12133.] |

Example 5: Experiment to Confirm Cancer Treatment Effect In Vivo

Figure 7:
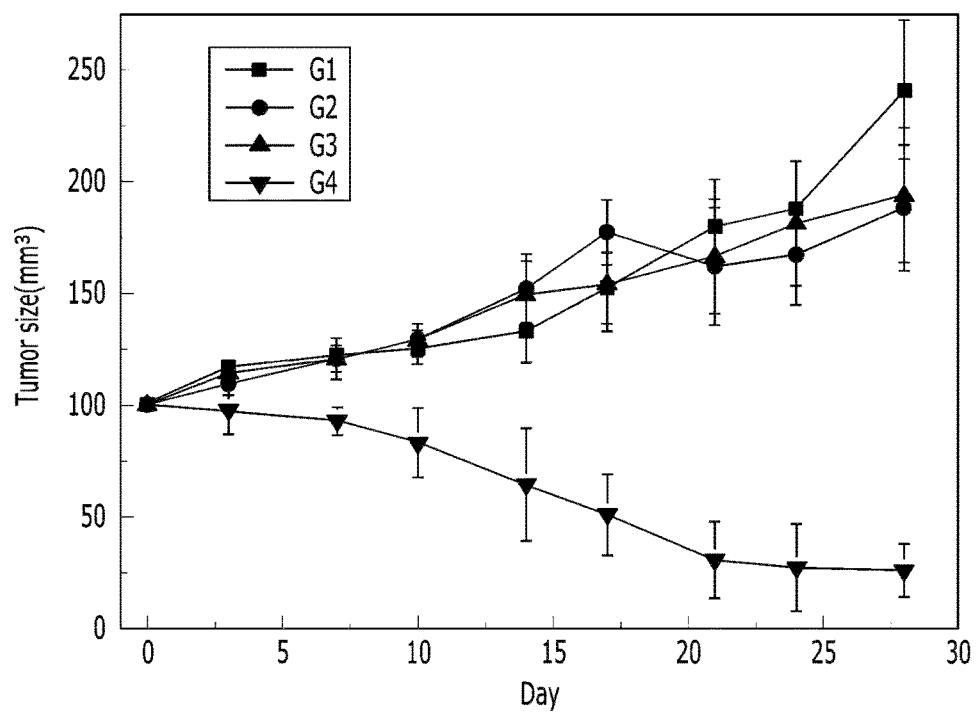
FIG. 7 is a graph showing the size of a cancer over time after performing an in vivo thermotherapy test using particles according to an embodiment of the present invention.

FIG. 7 shows that cell death by thermotherapy using the particles according to the present invention effectively occurs in vivo as well. Panc-1 cells were transplanted into a Balb/c nude mouse, and then when the size of cancer tissues became 100 mm3, a composition including the iron oxide magnetic particles of the present invention (150 µl of an aqueous solution obtained by dispersing 3 mg of magnetic particles having an iron oxide/CuI core/shell structure in deionized water) was subcutaneously administered. Thereafter, an alternating magnetic field generator (100 kHz, 80 G) was applied for 30 minutes to perform thermotherapy, and the volume of a cancer was observed for 28 days. As a result, the volume of the cancer was 90% smaller than that of an induced control group (G1), so that it was confirmed that the growth of the cancer was effectively suppressed.

TABLE 2

| Group | Gender | Number of animals (Head) | Administered substance | Alternating magnetic field Generating device Applied or not | Route for administration | Dosage (µL/head) |
|---|---|---|---|---|---|---|
| G1 | F | 5 | — | N | — | — |
| G2 | F | 5 | Composition including iron oxide magnetic particles of Example 2 | N | Direct injection | Test substance: 150 |
| G3 | F | 5 | — | Y | — | — |
| G4 | F | 5 | Composition including iron oxide magnetic particles of Example 2 | Y | Direct injection | Test substance: 150 |

Example 6: Toxicity Test when Administered In Vivo

Table 3 shows blood biochemical and electrolyte values examined before and on Day 1, Day 7, Day 14, and Day 28 after administering 150 µl of the composition according to the present invention to a Balb/c nude mouse. There was no significant decrease and/or increase in numerical values. After an intravenous injection, hepatotoxicity indicators (ALP, ALT, and AST) were slightly increased, and as kidney toxicity indicators, Glucose decreased and Creatinine and K were increased, but returned to normal on Day 7 to Day 14.

TABLE 3

| Parameters | | Day | | | | |
|---|---|---|---|---|---|---|
| | | 0 | 1 | 7 | 14 | 28 |
| Albumin (g/dl) | Mean | 1.79 | 1.43 | 1.55 | 1.70 | 1.67 |
| | SD | 0.08 | 0.10 | 0.42 | 0.18 | 0.09 |
| ALP (U/L) | Mean | 480.10 | 242.56 | 321.42 | 485.52 | 389.50 |
| | SD | 46.8 | 40.2 | 64.6 | 121.0 | 36.3 |
| ALT (U/L) | Mean | 40.2 | 175.0 | 32.7 | 47.8 | 35.1 |
| | SD | 6.2 | 41.2 | 10.8 | 25.8 | 4.5 |
| AST (U/L) | Mean | 40.2 | 174.96 | 32.72 | 47.78 | 35.12 |
| | SD | 6.2 | 41.2 | 10.8 | 25.8 | 4.5 |
| T.Bil (mg/dl) | Mean | 0.12 | 0.10 | 0.12 | 0.12 | 0.12 |
| | SD | 0.02 | 0.02 | 0.05 | 0.03 | 0.02 |
| BUN (mg/dl) | Mean | 28.94 | 177.15 | 43.01 | 33.46 | 23.41 |
| | SD | 4.55 | 34.33 | 31.90 | 6.81 | 3.02 |
| Ca (mg/dl) | Mean | 8.68 | 9.76 | 8.02 | 9.02 | 9.30 |
| | SD | 0.69 | 1.69 | 1.75 | 0.74 | 0.28 |
| Creatinine (mg/dl) | Mean | 0.24 | 1.476 | 0.294 | 0.342 | 0.32 |
| | SD | 0.05 | 0.21 | 0.06 | 0.04 | 0.03 |
| Glucose (mg/dl) | Mean | 212.07 | 112.432 | 174.124 | 177.234 | 219.356 |
| | SD | 23.6 | 42.1 | 62.6 | 48.4 | 46.3 |
| Na (mmol/L) | Mean | 149.2 | 147 | 149.2 | 147.2 | 146.6 |
| | SD | 2.4 | 3.2 | 3.6 | 1.1 | 2.7 |
| K (mmol/L) | Mean | 4.52 | 8.06 | 6.36 | 5.62 | 5.64 |
| | SD | 0.1 | 2.2 | 1.0 | 0.9 | 1.1 |
| Cl (mmol/L) | Mean | 114.4 | 113 | 111 | 108.8 | 112 |
| | SD | 1.1 | 6.0 | 3.3 | 4.1 | 2.3 |

What is the claimed is:

1. A method for preparing iron oxide magnetic particles, the method comprising:
    (a) synthesizing a complex by reacting iron and sodium oleate and an amine compound;
    (b) synthesizing an iron oxide crystal nucleus by mixing the complex with 1-octadecene (ODE) and dibenzyl ether (DBE); and
    (c) forming a shell by mixing the iron oxide crystal nucleus and CuI with 1-octadecene (ODE) and dibenzyl ether (DBE) in an 1-octadecene (ODE) volume % of 50% to 75%.

2. The method of claim 1, wherein the amine compound comprises one or more selected from the group consisting of methylamine, ethylamine, propylamine, isopropylamine, butylamine, amylamine, hexylamine, octylamine, 2-ethylhexylamine, nonylamine, decylamine, laurylamine, pentadecylamine, cetylamine, stearylamine, and cyclohexylamine, dimethylamine, diethylamine, dipropylamine, diisopropylamine, dibutylamine, diamylamine, dioctylamine, di(2-ethylhexyl)amine, didecylamine, dilaurylamine, dicetylamine, distearylamine, methylstearylamine, ethylstearylamine, and butylstearylamine, triethylamine, triamylamine, trihexylamine and trioctylamine, triallylamine and oleylamine, laurylaniline, stearylaniline, triphenylamine, N,N-dimethylaniline and dimethylbenzylaniline, monoethanolamine, diethanolamine, triethanolamine, dimethylaminoethanol, diethylenetriamine, triethylene Tetramine, tetraethylenepentaamine, benzylamine, diethylaminopropylamine, xylylenediamine, ethylenediamine, hexamethylenediamine, dodecamethylenediamine, dimethylethylenediamine, triethylenediamine, guanidine, diphenylguanidine, N,N,N',N'-tetramethyl-1,3-butanediamine, N,N,N',N'-tetramethylethylenediamine, 2,4,6-tris(dimethylaminomethyl)phenol, morpholine, N-methylmorpholine, 2-ethyl-4-methylimidazole and 1,8-diazabicyclo (5,4,0)undecene-7 (DBU).

3. The method of claim 1, wherein the iron oxide comprises one or more selected from the group consisting of Fe13O19, Fe3O4 (magnetite), γ-Fe2O3 (maghemite), and α-Fe2O3 (hematite), β-Fe2O3 (beta phase), ε-Fe2O3 (epsilon phase), FeO (Wüstite), FeO2 (Iron Dioxide), Fe4O5, Fe5O6, Fe5O7, and Fe25O32.

4. The method of claim 1, further comprising coating the surface of particles prepared after Step (c) with a hydrophilic ligand.

5. The method of claim 4, wherein the hydrophilic ligand comprises one or more selected from the group consisting of polyethylene glycol, polyethylene amine, polyethylene imine, polyacrylic acid, polymaleic anhydride, polyvinyl alcohol, polyvinylpyrrolidone, polyvinyl amine, polyacrylamide, polyethylene glycol, phosphate-polyethylene glycol, polybutylene terephthalate, polylactic acid, polytrimethylene carbonate, polydioxanone, polypropylene oxide, polyhydroxyethyl methacrylate, starch, dextran derivative, sulfonic acid, amino acid, sulfonic acid peptide, silica, and polypeptide.

* * * * *